(12) United States Patent
Heeres et al.

(10) Patent No.: US 10,927,498 B2
(45) Date of Patent: *Feb. 23, 2021

(54) PROCESS FOR THE PREPARATION OF AROMATIC COMPOUNDS

(71) Applicant: Huntsman International LLC, The Woodlands, TX (US)

(72) Inventors: André Heeres, Groningen (NL); Niels Jan Schenk, Groningen (NL); Arend-Jan Zeeuw, Wassenaar (NL); Bart De Waele, Heverlee (BE); Kornelis Jan Kamminga, Bedum (NL)

(73) Assignee: HUNTSMAN INTERNATIONAL LLC, The Woodlands, TX (US)

( * ) Notice: Subject to any disclaimer, the term of this patent is extended or adjusted under 35 U.S.C. 154(b) by 484 days.

This patent is subject to a terminal disclaimer.

(21) Appl. No.: 15/508,963

(22) PCT Filed: Sep. 22, 2015

(86) PCT No.: PCT/EP2015/071655
§ 371 (c)(1),
(2) Date: Mar. 6, 2017

(87) PCT Pub. No.: WO2016/046163
PCT Pub. Date: Mar. 31, 2016

(65) Prior Publication Data
US 2018/0237989 A1  Aug. 23, 2018

(30) Foreign Application Priority Data
Sep. 22, 2014 (EP) ..................................... 14185750

(51) Int. Cl.
*D21C 11/12* (2006.01)
*C10G 3/00* (2006.01)
(Continued)

(52) U.S. Cl.
CPC ............. *D21C 11/125* (2013.01); *B01J 29/40* (2013.01); *B01J 29/89* (2013.01); *B01J 35/10* (2013.01);
(Continued)

(58) Field of Classification Search
CPC ...... D21C 11/12; D21C 11/122; D21C 11/127
See application file for complete search history.

(56) References Cited

U.S. PATENT DOCUMENTS 5,504,259 A    4/1996  Diebold et al.
8,945,424 B2 * 2/2015  Pansare .................... B01J 21/04
                                                    252/373

(Continued)

FOREIGN PATENT DOCUMENTS

WO    2014146128 A1    9/2014

OTHER PUBLICATIONS

Bhattacharya et al., Pyrolysis of Black Liquor Solids, 1986, Ind. Eng. Chem. Process Dex. Dev, 25, p. 420-426. (Year: 1986).*

(Continued)

*Primary Examiner* — Anthony Calandra
(74) *Attorney, Agent, or Firm* — Huntsman International LLC; Robert Diaz

(57) ABSTRACT

A process for the preparation of small aromatic compounds from black liquor comprising:
  providing black liquor that derives from alkaline treatment of wood chips;
  subjecting the black liquor to a pyrolysis treatment to yield a pyrolysed black liquor gas and a solid mass comprising char and salts in a first reactor, wherein the salts substantially derive from the treatment of black liquor;
  contacting at least part of the pyrolysed black liquor gas with a catalyst in a second reactor, which is different (Continued)

from the first reactor to provide a conversion treatment to yield a conversion product; and recovering small aromatic compounds from the conversion product.

16 Claims, 4 Drawing Sheets

(51) Int. Cl.

| | |
|---|---|
| *C10G 1/00* | (2006.01) |
| *B01J 29/40* | (2006.01) |
| *B01J 29/89* | (2006.01) |
| *B01J 35/10* | (2006.01) |
| *B01J 37/00* | (2006.01) |
| *C07C 4/16* | (2006.01) |
| *C07C 4/18* | (2006.01) |
| *D21C 11/00* | (2006.01) |
| *D21C 11/06* | (2006.01) |

(52) U.S. Cl.
CPC ............. *B01J 37/0009* (2013.01); *C07C 4/16* (2013.01); *C07C 4/18* (2013.01); *C10G 1/002* (2013.01); *C10G 3/40* (2013.01); *C10G 3/49* (2013.01); *D21C 11/0092* (2013.01); *D21C 11/063* (2013.01); *C07C 2529/40* (2013.01); *C07C 2529/85* (2013.01); *C07C 2529/89* (2013.01); *C10G 2300/1003* (2013.01); *C10G 2300/1014* (2013.01); *C10G 2400/30* (2013.01); *Y02P 20/582* (2015.11); *Y02P 30/20* (2015.11)

(56) References Cited

U.S. PATENT DOCUMENTS

| | | | |
|---|---|---|---|
| 10,184,213 B2* | 1/2019 | Zeeuw | D21C 11/12 |
| 2007/0169412 A1* | 7/2007 | Sinquefield | B01J 27/043 |
| | | | 48/127.9 |
| 2010/0121126 A1* | 5/2010 | Northrop | C10G 70/046 |
| | | | 585/821 |
| 2011/0272108 A1* | 11/2011 | Prochazka | D21C 3/022 |
| | | | 162/38 |
| 2012/0029243 A1 | 2/2012 | Pantouflas et al. | |
| 2013/0232852 A1 | 9/2013 | Peterson et al. | |
| 2013/0324772 A1 | 12/2013 | Huber et al. | |
| 2014/0206913 A1 | 7/2014 | Mazanec et al. | |
| 2016/0030931 A1 | 2/2016 | Kelkar et al. | |

OTHER PUBLICATIONS

Corma et al., Zeolite Beta:Structure, Activity, and Selectivity for Catalytic Cracking, 1988, ACS Symposium Series, chapter 4 p. 49-63. (Year: 1988).*

Acton Asoton, Silicates—Advances in Research and Application, 2013, p. 59-60 (Year: 2013).*

* cited by examiner

PROCESS FOR THE PREPARATION OF AROMATIC COMPOUNDS

CROSS-REFERENCE TO RELATED APPLICATIONS

This application is the National Phase of International Application PCT/EP2015/071655 filed Sep. 22, 2015 which designated the U.S. and which claims priority to European App. Serial No. 14185750.8 filed Sep. 22, 2014. The noted applications are incorporated herein by reference.

The present invention relates to a process for the preparation of small aromatic compounds from black liquor.

Small aromatic compounds such as benzene, toluene, xylenes and naphthalenes, represent valuable starting materials for a large number of applications. Mixtures of such compounds can be found in aromatic fuels, including gasoline. Benzene may further be used as chemical intermediate, e.g. in the production of ethyl benzene, cumene and cyclohexane. Toluene has found application as a solvent, e.g. for paints, printing ink and glues. It is also used as chemical intermediate in the preparation of toluene diisocyanate, which is a starting material for the production of polyurethane foams. Further it may be used in its disproportionation to benzene and xylenes. p-Xylene is used in the preparation of terephthalic acid, which is a monomer for several plastics, such as aramid and polyesters, such as polyethylene terephthalate (PET). o-Xylene is mainly used in the production of plasticizers for PVC. The main market for naphthalenes resides in the preparation of phthalic acid.

Currently, these aromatic compounds are produced via refinery processes of fossil fuels. Common processes include steam cracking, steam reforming and catalytic reforming. In order to arrive at a more environmentally friendly and sustainable production of these aromatic compounds, research has been carried out in identifying different, more sustainable starting materials for the production thereof. Such suitable starting materials include refuse and biomass and mixtures thereof.

It has been found that black liquor, coming from a paper pulp process, can be used as basis to provide valuable compounds. In a paper pulp process, wood chips are treated in a digester system to separate the cellulose fibers and to remove lignin, which binds the fibers together in the natural state of wood. Digestion of wood chips using heat and chemicals is a common practice in the industry. In this process, for instance the Kraft process, commonly wood chips and alkaline digesting liquor are introduced to a digester creating pulp and a lignin containing soluble part, also called black liquor. After the digestion process the produced pulp and the black liquor are separated to be further treated separately. The pulp comprises cellulose fibers and is typically treated further to make paper. The black liquor comprises lignin, hemicelluloses, inorganic salts, and other extractive components. Black liquor is often concentrated by removing the water content to obtain black liquor with a solid weight content of between 70 and 90 wt %. The concentrated black liquor is also called "strong black liquor". The concentration of the solid content of black liquor is a process which is being done in most of the existing paper mills. Part of the (strong) black liquor can be treated further by burning it in specific recovery boilers for energy production and recovering of the salts resulting from the digestion process. The salts can be used to remake chemicals required in the paper pulp process. Strong black liquor appears to be better to recover salt. It has been found that at least a part of the black liquor can be used for obtaining energy and valuable compounds. Research has been done in the past to provide syngas that can be converted to automotive fuel production and other compounds such as alcohols, alkanes, alkenes and ethers. Also the valorization of (Kraft) lignin, the major constituent of black liquor and which is separated from black liquor, to valuable compounds that can be used for fuel or other applications has been investigated.

It is an object of the present invention to provide a process for producing small aromatic compounds that can be used on an economical valuable way, on an industrial scale, on a continuous way and, which can be integrated in other existing plants such as a paper mill plant.

It is a further object of the present invention to provide small aromatic compounds from black liquor, using a process that can be integrated in an existing paper mill, in a way that e.g. energy and salts still can be recovered for further use in the paper industry.

In addition, it is an object to obtain small aromatics that are substantially free from oxygen atoms.

These objects are met, at least partially, by a process according to claim 1.

Accordingly, the present invention provides a process for the preparation of small aromatic compounds from black liquor comprising:

providing black liquor that derives from alkaline treatment of wood chips;

subjecting the black liquor to a pyrolysis treatment to yield a pyrolysed black liquor gas and a solid mass comprising char and salts in a first reactor, wherein the salts substantially derive from the treatment of black liquor;

contacting at least part of the pyrolysed black liquor gas with a catalyst in a second reactor, which is different from the first reactor to provide a conversion treatment to yield a conversion product; and recovering small aromatic compounds from the conversion product.

The inventors found that pyrolysing black liquor provides pyrolysed black liquor gas that can be treated further catalytically in a second reactor and provides small aromatic compounds. Further, the inventors surprisingly found that no initial separation of certain compounds, such as lignin, is required and can be used as such in the process of the invention to obtain a sufficiently high yield of small aromatic compounds. In addition, the pyrolysis treatment is provided without the addition of a catalyst. The inventors surprisingly found that pyrolysing black liquor without using a catalyst, provides black liquor gas that can be treated further catalytically in a second reactor and provides small aromatic compounds. If a catalyst such as a zeolite catalyst would be present during the pyrolysis, the high amounts of inorganic salts present in black liquor could interfere with the catalysts and would negatively influence the activity. Furthermore, the inventors surprisingly found that the process according to the invention provides a higher yield of small aromatic compounds compared with other biomass sources such as wood. In addition, the process according to the invention also provides a higher yield of small aromatic compounds than with lignin. This is especially the case when the black liquor is used that is derived from hardwood.

Also, it has been found that most of the aromatic compounds that are formed are no longer substituted with oxygen atoms.

In addition, the process can be performed on a plant of paper pulping and the energy released during processing of the black liquor can be recovered and be used in processing the black liquor or in the process for separating paper pulp from black liquor. The solid mass comprising char, which is produced during pyrolysis, can be considered as a waste product when the aim is to make small aromatic compounds. However, the inventors surprisingly found that the solid mass comprising salt and char produced during pyrolysis of the black liquor and/or in the conversion treatment can be collected to recover salt. This salt is required to make new pulp. Substantially all the salt in the solid mass derives from the process of making black liquor. The char comprises a lot of energy which is converted in the recovery boiler and assists the recovery of the salt. The inventors thus found a process where there is a balance between upgrading black liquor to valuable small aromatic compounds, while the produced char is still valuable for further use in the paper mill industry.

According to this invention "black liquor" is the soluble part that is present after wood chips have been treated with the Kraft or Soda anthraquinone (Soda-AQ) process. In these processes the black liquor derives from alkaline treatment of wood chips. This can be done by the well known Kraft process by using a basic mixture of sodium hydroxide and sodium sulfide. When the well known "soda aq" process is used to make the black liquor, sodium hydroxide is used. Anthraquinone (aq) can be used as a pulping additive to decrease the carbohydrate degradation. In both the soda aq process and the Kraft process also additional salts can be added such as potassium salts of sulfide, sulfate, thiosulfate, sulfite, carbonate, chloride, lignate, soaps and sugar acids and/or silicate. Also lesser amounts of calcium, magnesium salts can also be found, probably as organic complexes. The salt can also comprise traces of host of other cations, and silica. The alkaline solution used for the alkaline treatment is added to the wood chips, which are digested in a digester so that the bonds that link lignin to the cellulose break. This results in cellulose pulp, which is insoluble in the basic environment, and a liquid, the black liquor. Black liquor comprises lignin, lignin fragments, hemicellulose, carbohydrates from the breakdown of hemicellulose, sodium carbonate, sodium sulfate and other inorganic salts and water. The salt in the black liquor substantially derives from the alkaline treatment of the wood chips.

Typically, black liquor has 15 wt % solids by weight. However, preferably strong black liquor is used in the invention, where the solids concentration is between 70 wt % and 90 wt %. When in the description is referred to black liquor, this may also apply to "strong black liquor" unless it is otherwise specified.

In one embodiment, the black liquor is derived from hardwood or softwood. Most preferably, the black liquor is derived from hardwood. Hardwood is wood from angiosperm trees. A suitable example of hardwood is wood coming from poplar, amongst which hybrid poplar. Softwood is wood from gymnosperms trees. Suitable examples of softwood are wood coming from pines.

According to this invention, small aromatic compounds are mono-aromatic compounds comprising one aromatic ring, which can be substituted, and oligomeric aromatic compounds comprising two or three aromatic ring structures, which can be substituted. Examples of the small aromatic compounds are benzene, toluene, ortho-xylene, meta-xylene and para-xylene, trimethylbenzene, ethylbenzene, diethylbenzene, triethylbenzene. An example of oligomeric aromatic compound is naphthalene, which can be substituted.

In one embodiment, the temperature during the pyrolysis treatment is sufficiently high so that the black liquor pyrolyzes. Pyrolysis in this context means a thermo-chemical process, wherein the heat is introduced into the process substantially via a solid substrate where no external oxygen is present and through the heat the black liquor decomposes. Preferably the temperature during the pyrolysis is sufficiently low so that the solid substrate remains solid and the salts present in the solid substrate do not melt. Preferably, the pyrolysis treatment of black liquor is carried out at a temperature of 350° C. to 700° C. and/or at a pressure of 0.1 to 6 bara.

The pyrolysis occurs in a first reactor which is different from the second reactor. During pyrolysis, no catalyst is added to the first reactor, except for the material (such as salt) that is already present in the black liquor due to the preparation of the black liquor. It might be possible that the salts present in the black liquor have a catalytic activity during the pyrolysis.

Preferably, the black liquor flows through the pyrolysis reactor at a high velocity so that the solid substrate swirls around in the reactor. Preferably, fluidizing gas is added to the reactor at a high velocity so that the black liquor and the solid substrate fluidize in the reactor. The fluidizing gas is preferably an inert gas such as $N_2$. Preferably, non inert gasses such as air, $O_2$, $H_2O$ are avoided during the pyrolysis since these can cause secondary reactions. However, small leakage of such gasses in the reactor installation may occur, which only would cause secondary reactions of minor significance.

Through the heat, the black liquor pyrolyzes and decomposes in char and pyrolysed black liquor gas. The char is part of the solid mass which can be further used as a solid substrate. The pyrolysed black liquor gas flows through the reactor and the solid mass becomes entrained in the pyrolysed black liquor gas flow. Subsequently the solid mass and the pyrolysed black liquor gas can be separated. This can be done by any known method to separate a gas from a solid. Such methods include filtering, electrostatic separation and separation by inertia or a combination thereof. Preferably the first separation of the gas is performed using inertia. This technique is based on the recovery of solid particles by a change of direction of the solids-containing gas flow. This can be achieved by static separators. However, this is commonly better obtained by using centrifugal forces, e.g. in one or more cyclones.

As described, preferably the solid mass obtained after pyrolysis comprising char and salt, is collected and can be used in the recovery boiler.

It has been found that the pyrolysed black liquor gas comprises syngas (i.e. CO, $CO_2$, $H_2$), hydrocarbons with olefinic unsaturation, organic and aromatic compounds that contain oxygen, such as phenols, methoxyphenols and to a minor extent ketons, alcohols, ethers such as furanics, carboxylic acids etc., which compounds may be originating from the (hemi)cellulose fraction present in black liquor. As described, the inventors found that these compounds and other compounds in the pyrolysed black liquor gas can be converted into small aromatic compounds. After pyrolysis, the pyrolysed black liquor gas is contacted with a catalyst in a second reactor to provide a conversion treatment to yield a conversion product. The contact of the pyrolysed black liquor gas with the catalyst can occur in a reactor which is in connection with the pyrolysing reactor, e.g. through pipes. Preferably, the pyrolysed black liquor gas is contacted with the catalyst directly after the pyrolysis step, optionally after separation, without first being stored and/or cooled down.

This prevents that secondary reactions would occur in the pyrolysed black liquor vapours during storage, or cooling and reheating.

It has been found that the catalytic conversion treatment involves the conversion of complex aromatic compounds to small aromatic compounds, the conversion of oxygen containing aromatic and oxygen containing aliphatic compounds to small aromatic compounds without oxygen atoms, and the conversion of hydrocarbons, such as olefins into small aromatic compounds.

Preferably, a zeolitic catalyst is used. Preferably, the catalyst is selected from aluminosilicates, SAPOs (Silicoaluminophosphates), silicalites and combinations thereof. It has been found that the catalyst preferably is acidic. The acidity may be influenced by the structure of the aluminosilicate and also by the ratio between silicate moieties and aluminate moieties in the aluminosilicate. The acidity may e.g. be accomplished by ion exchange catalyst with ammonium salts and subsequent calcination thereof. The silica alumina ratio (SAR) is relevant for the potential acidity of the catalyst. At a low SAR and if virtually all the active sites have been rendered in the H+ form, the resulting catalyst is very acidic. Suitable SARs include those in the range of 5 to 300, preferably, from 10 to 150, more preferably from 20 to 90, e.g. 23, 45 or 80. Another feature that may play a role in the performance of the catalyst is the pore diameter. It has been found that particularly good results are obtained if the largest internal pore size of the catalysts is in the range of 4.5 to 12 Å, preferably from 5 to 7 Å. A person skilled in the art knows that the catalyst can have different pore dimensions. Without being bound to a theory, it is has been thought that the pores of the catalyst form cages wherein the pyrolysed black liquor gas molecules can enter. The molecules are only able to "escape" the cages when they are reduced in size. Bigger aromatics may be so converted to small aromatic compounds, and aromatics having longer substituted groups, such as oxygen containing groups, are so forced to remove the substituents.

The catalyst is preferably a zeolite that is selected from the group consisting of ZSM-5, ZSM-11, ZSM-35, ZSM-23, ferrierite, zeolite beta, zeolite Y, zeolite X, mordenite, zeolite A, IM-5, SSZ-20, SSZ-55, MCM-22, TNU-9, NU-87, ZSM-57, ZSM-48, EU-1, SSZ-35, SSZ-44, Utrastable Y (US-Y), SBA-15, AL-SBA15, ZSM-18, LZ-135, ZSM-10, MCM-68, SSZ-57, ECR-1, ITQ-25, COK-14, MOR, ZSM-12 SSZ-48 and combinations thereof. The most preferred catalysts are ZSM-5, zeolite Y, Beta and ZSM-23 or combinations thereof. Preferred combinations are zeolite beta and ZSM-5; and zeolite Y and ZSM-5. When combinations of catalysts are use, they can have a different acidity.

As indicated above, the acidity of the catalyst plays a role in the conversion of the pyrolysed black liquor gas. The acidity may be related to the silica alumina ratio of the catalyst when the catalyst is a zeolitic catalyst. When the catalyst is a zeolitic catalyst also the pore size of the zeolite catalyst is a factor in the process according to the present invention. Good results have been obtained by using a ZSM-5 catalyst having an acidity of 23, 45 or 80.

The conversion treatment can also be carried out when additives are added to the catalyst. Phosphor can be used to increase the hydrothermal stability of the catalyst. Also other trivalent rare earth elements can be used (e.g. europium). The catalyst can also have an acidity gradient that changes in function of the distance to the zeolite surface and can be more or less acidic at the surface versus the core of the catalyst. The gradient can be a consequence of synthesis procedure or post synthesis treatment, e.g. treatment of the catalyst with steam.

The conversion treatment is suitably carried out at a temperature in the range of 200 to 1000° C. Relatively high temperatures, such as 350 to 650° C. are preferred since they tend to increase the formation of aromatic compounds from the vaporous phase. The pressure suitably ranges from 1 to 4 bara. In the conversion treatment the catalyst is suitably present in a weight ratio of pyrolysed black liquor gas to catalyst in the range of 5:1 to 1:20, and more preferably in the range of 1:1 to 1:5.

The catalyst can form together with a binder bound catalyst. The binder gives the catalyst strength. The binder can be selected from inorganic refractory oxides, in particular alumina, silica, silica alumina, titania, zirconia, kaolin and mixtures thereof. In addition to the provision of mechanical strength, the binder can have a positive effect on the catalyst performance.

When a binder is used, the amount of the binder in such combinations may vary within wide ranges. Suitably the amount of binder in a catalyst is in the range of 0 to 80% wt, preferably, 40 to 70% wt, based on the total weight of the catalyst comprising the binder. Such a ratio provides a bound catalyst with a satisfactory mechanical strength.

The catalytic conversion treatment of the present process may be carried out in a fixed bed. The pyrolysed black liquor gas may in this case be passed through the bed in an up-flow or a down-flow direction. However, since the conversion to aromatic compounds may result in some coke deposition on the catalyst, a gradual deactivation may take place in such a fixed bed. Therefore, it is also possible to conduct the conversion treatment in a moving or fluidized bed. In a fluidized bed the catalyst is continuously added and passed in a fluidized way to an exit whilst being surrounded by vapors. The vapors comprise initially the vapors from the pyrolysed black liquor gas (which comprise phenols and other oxygenated compounds) and will be converted over time to small aromatic compounds that are largely deoxygenated. Then the catalyst is separated from the vapors and may then be passed to a regenerator where it is subjected to contact with an oxygen-containing gas to remove any coke that is deposited on the catalyst. The skilled person will be familiar with the concept of catalyst regeneration in a fluid bed arrangement. The regeneration is more effective when the catalyst is impregnated with metal.

The catalyst that is thus regenerated may, typically continuously, be recycled to the conversion treatment.

After the catalytic conversion treatment, a conversion product is formed which comprises small aromatic compounds such as benzene, toluene, xylene and/or naphthalene. In addition, when a zeolite catalyst, such as the H-ZSM-5, is used the small aromatic compounds mainly comprise oxygen free small aromatics. The conversion products are substantially free from phenols and other aromatic compounds comprising oxygen atoms.

The small aromatic compounds are then recovered from the conversion product. The skilled person will realize that it is feasible to recover the various aromatic compounds separately. Alternatively, it is feasible to recover all aromatic compounds in one fraction. The skilled person will adopt the desired level of fractionation in accordance with the needs and uses of the aromatic compounds.

The conversion product does not consist solely of small aromatic compounds. It also contains some by-products, such as olefins. It is sometimes desired to recover the olefins separately from the aromatic compounds. Also other byproducts, such as alkanes, such as methane, hydrogen, carbon monoxide, carbon dioxide and water may be present. Therefore, the conversion product is preferably subjected to fractionation, yielding small aromatic compounds as a separate fraction or fractions, such as a BTX fraction and a fraction comprising other small aromatic compounds, optionally one or more olefin fractions, and a residue.

The residue may be combusted to yield energy for the heating of the various feed streams and intermediate products. At least part of the one or more olefin fractions may be recycled to the catalytic conversion treatment. It is also possible to recycle at least part of the one or more olefins fractions to the pyrolysis treatment. Also, at least part of the olefins fraction may be recycled to the conversion treatment and to the pyrolysis treatment. At least part of the one or more olefins fractions may be recycled to either one of the pyrolysis treatment and the conversion treatment or to both. Furthermore, the residue can also be catalytically converted to a second conversion product enriched in small aromatic compounds in a follow-up reactor. Gasses such as water gas and alcohols in gas form can be added to the residue which may help in forming the small aromatic compounds.

The yield on small aromatic compounds can be increased further by the addition of extra reactants to the conversion treatment. Such extra reactants can suitably be selected from the group consisting of extra olefins, alcohols, aldehydes, ketones, acids and combinations thereof. The extra reactants suitably have from 1 to 6 carbon atoms. Examples of suitable extra reactants include hydrogen, butane, isobutene, pentenes and hexenes, methanol, ethanol, propanol or iso-propanol and hexanol, formaldehyde and acetaldehyde, acetone, methyl ethyl ketone, formic acid and acetic acid.

A suitable method for recovering the aromatic compounds from the conversion product is constituted by a method wherein the conversion product is passed into an extraction column. A liquid hydrocarbon is sprayed into the conversion product thereby cooling the conversion product and providing a solvent for the aromatic compounds. Oxygen containing compounds, such as formic acid, propionic acid, etc., including water that may be formed during the process, easily separate from the mixture of conversion product and liquid hydrocarbon. In this way the aromatic hydrocarbons are recovered together with the liquid hydrocarbon. After separation of the liquid hydrocarbon phase that contains the aromatic compounds from the phase that comprises oxygen-containing compounds, including water, the liquid hydrocarbon phase is suitably subjected to fractionation to obtain the small aromatic compounds.

Accordingly, the present invention also provides a method for recovering aromatic compounds from a vaporous stream that comprises the aromatic compounds and oxygen containing compounds, such as the conversion product, which method comprises contacting the vaporous stream with a liquid hydrocarbon absorbent to obtain a hydrocarbon phase containing aromatic compounds, and an oxygen-containing compound phase, and separating the hydrocarbon phase from the oxygen-containing compound phase. The aromatic compounds can be suitably recovered from the hydrocarbon phase via any known method, including fractionation. The liquid hydrocarbon absorbent can be aliphatic, cycloaliphatic or aromatic. The use of aliphatic or cycloaliphatic hydrocarbons has the advantage that the separation of the aromatic compounds can be made and it can easily be determined what the yield of aromatic compounds from the feed is. If aromatic hydrocarbons are used as liquid hydrocarbon absorbents, the advantage is that no extraneous products need to be used in the process. The aromatic hydrocarbons that are used for this purpose may be the product from the conversion earlier. That would mean that a fraction of the aromatic compounds that have been separated from the conversion product can be used to extract further aromatic compounds from the conversion product. That has the advantage that no additional fractionation to recover the extraction solvent, i.e. the liquid hydrocarbon, separately is needed. The liquid hydrocarbon is suitably selected from the hydrocarbons containing from 6 to 12 carbon atoms. The temperature and pressure can be selected by the skilled person according to his desires.

The invention will be further elucidated by means of the following examples and figures.

EXAMPLES

1. Pyrolysis from Black Liquor and Subsequent Conversion of Pyrolysed Black Liquor Gas Via a Gram Scale Reactor Unit Black liquor was obtained from a standard Kraft process using *Eucalyptus* wood as the predominant feed and was freeze dried (BLFD). The BLFD is first pyrolysed and subsequently up-graded using a gram-scale reactor set up comprising a pyrolysing unit and an up-grading unit, which are connected with each other. A constant stream of N2 of 7 min/ml was used as a gas flow in order to maintain an inert atmosphere. The pyrolysing unit was filled with about 1.5-2.0 g BLFD and the upgrading unit was filled with about 10 gram of H-ZSM-5 catalyst. The gram-scale reactor set up was placed in a fluidized sand bed (T=510° C.) in a way that the upgrading unit is placed first in the fluidizing bed, so that the unit becomes 510° C. and then the pyrolysing unit comprising the BLFD was brought in the fluidizing bed so that the pyrolysis starts at a temperature of 510° C. The pyrolysis takes about 1.5-15 min. The pyrolysis reaction induces an increasing gas flow due to the gasses that are produced. The pyrolysis is finished from the moment that the gas flow has again about the same flow as the initial N2 flow. The obtained pyrolysed black liquor gas is subsequently converted in the upgrading unit via catalytic treatment. The converted pyrolysed black liquor gas was subsequently condensed by bringing the gas to a temperature of −15° C. in a cooling unit. The cooling unit was then washed with small amounts of petroleum ether (pet-ether). Through a phase separation of the condensate, the water layer was separated from the organic layer. The water layer amounts to 20.1 wt % based on the weight of BLFD. The amount of condensed and converted pyrolysed black liquor which remains in the organic phase amounted to 20.2 wt % based on the weight of BLFD.

Figure 1:
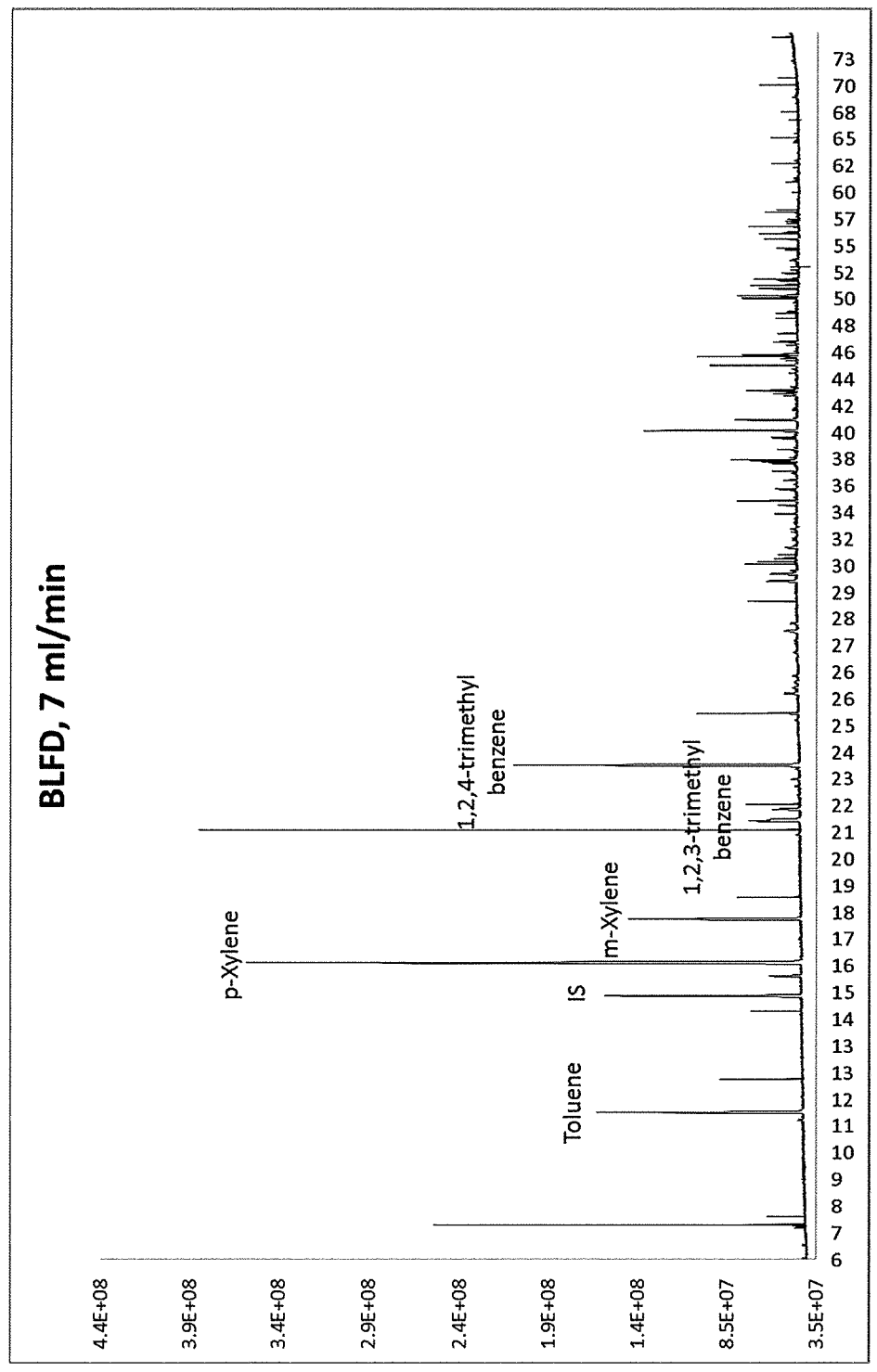
FIG. 1 shows a chromatographic diagram of the chromatography of pyrolysed black liquor gas that has been treated with a catalyst in a gram scale experiment.

FIG. 1 shows a gas chromatographic analysis of the separated organic layer, which is thus freeze-dried black liquor pyrolysed at 510° C. and that is catalytically converted and than condensed. In order to exclude for large quantities pet-ether present, the chromatogram only shows peaks arising after 4 minutes.

As shown in FIG. 1, GC-MS analysis shows that the black liquor can be converted to small aromatic compounds such as benzene, toluene and xylene.

2. Aromatics Derived from Pyrolysing Black Liquor which is Subsequent Converted Using an Auger Reactor Black liquor was obtained from a standard Kraft process using *Eucalyptus* wood as the predominant feed. Pyrolysis experiments of black liquor were carried out in a continuously operating mini-plant using Auger reactor technology. Under an inert atmosphere (N2 flow of 125 ml/min) black liquor (218 ml, 390 gram, total solids 71.7%) is fed into the pyrolysis reactor and intensively mixed with sand at a temperature of 500° C. Subsequently the pyrolysed black liquor vapors were contacted under a continuous N2 stream with a pre-heated fixed bed catalyst mixture (280 gram H-ZSM-5(23)) at T=550° C. for further conversion. The obtained conversion product is condensed at T=−15° C., followed by cooling with a subsequent cold trap (liquid nitrogen, T=−196° C.). All condensate units were washed with an organic solvent (pet-ether) in order to collect all condensates. The organic layer was separated from the water layer and concentrated on a rotavap (yield 2.70 g, not optimized).

Figure 2:
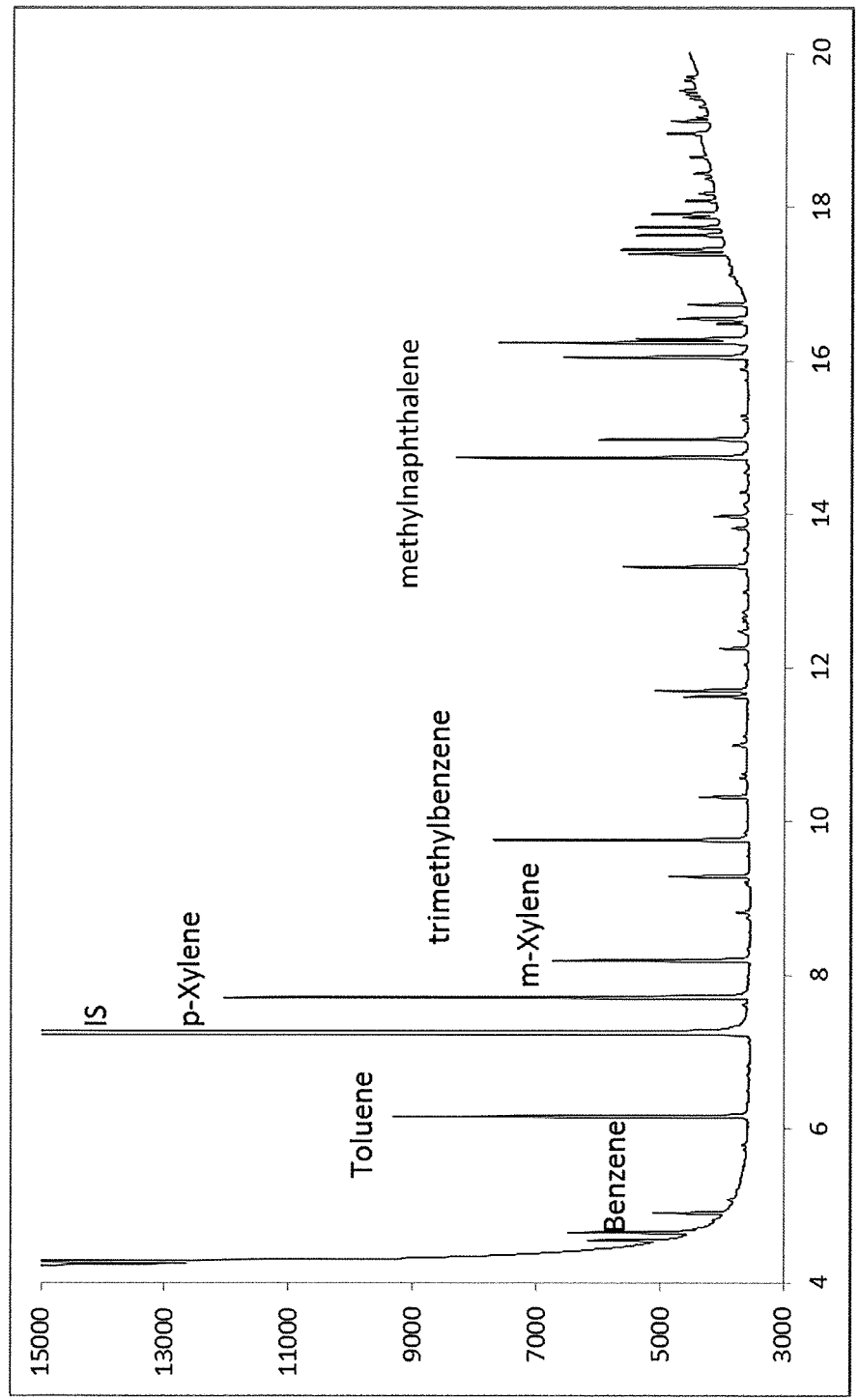
FIG. 2 shows a chromatographic diagram of the chromatography of pyrolysed black liquor gas that has been treated with a catalyst in an auger reactor.

FIG. 2 shows a gas chromatographic diagram of pyrolysed black liquor in pet-ether that has been treated with an H-ZSM-5 catalyst according to the above-described procedure performed in an auger reactor. Besides the monoaromatics benzene (Rf=4.90), toluene (Rf=6.16), p-xylene (7.71), o,m-xylene (8.18) also higher aromatics are being formed under the conditions used.

Figure 3:
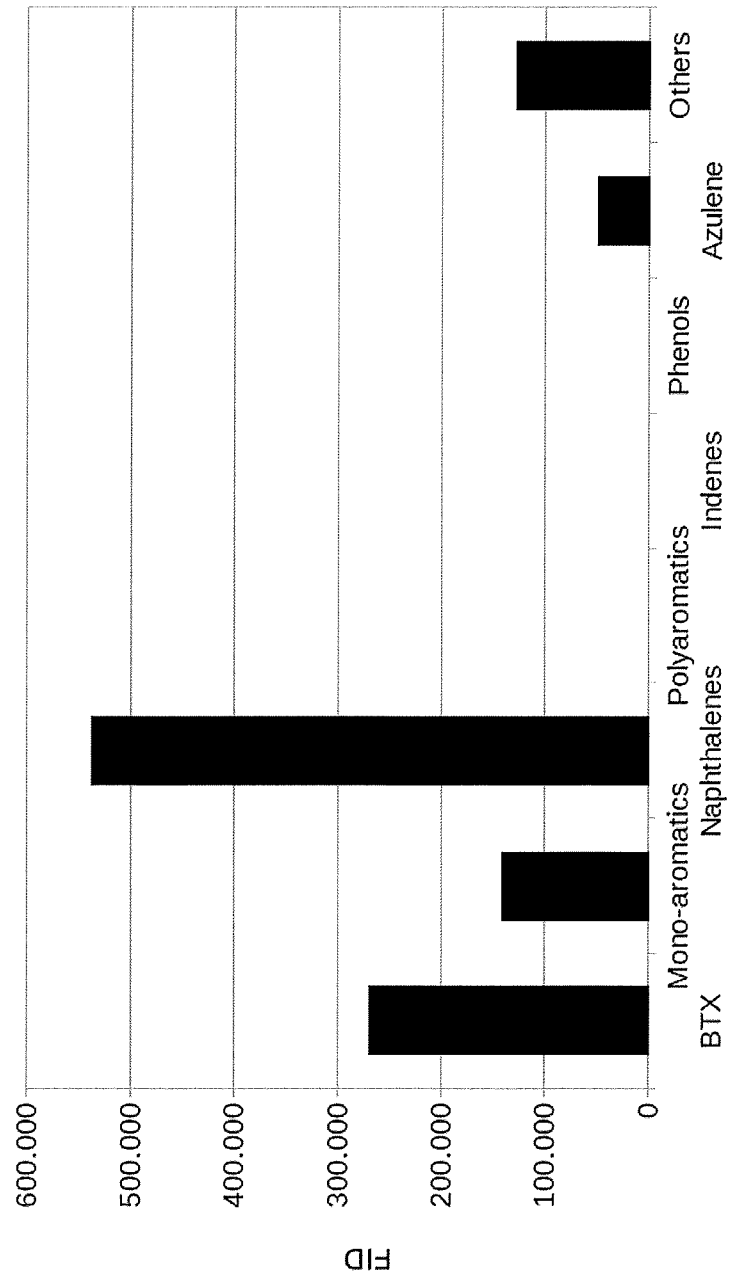
FIG. 3 shows the Flame ionization detector (FID) analysis obtained in gas chromatographic analysis providing the relative amount of benzene, toluene, xylene (BTX); other mono-aromatics; naphtalenes; azulenes and other aromatic compounds.

FIG. 3 depicts, based upon the FID values obtained in the GC analysis, the ratio between BTX (benzene, toluene, xylenes), other mono-aromatics, naphtalenes, azulens and other aromatic compounds under the reaction conditions formed.

3. Black Liquor Derived from Hardwood Compared with Other Biomass Sources

Several sources of biomass where treated. Kraft Northern/Southern Hardwood, is black liquor prepared using the Kraft treatment of hardwood chips. Soda Southern Hardwood is black liquor prepared using the soda aq treatment of hardwood wood chips.

Hybrid poplar is wood chips coming from hardwood hybrid poplar.

Pinewood is wood chips coming from a pine tree.

Kraft lignin is lignin derived from black liquor that was prepared by Kraft treatment.

The biomass sources were all treated in the same way using a Frontier Lab tandem micro reactor model (RX-3050TR) equipped with a single shot sampler (PY1-1040), that is mounted on a gas chromatograph-mass spectrometer (GC-MS). The first reactor pyrolyzes the biomass at 500° C. The pyrolysed biomass gas coming from the first reactor is converted in a second different reactor comprising H-ZSM-5 catalyst at 600° C. The pyrolysis reactor is loaded with 1.0-1.5 mg of black liquor. The catalyst reactor is loaded with approximately 8 mg of catalyst. The catalyst is used for several subsequent experiments without regeneration. The converted pyrolysed black liquor gas was immediately analyzed by the GC-MS.

Analysis of the products were performed by a gas chromatograph (GC) using a Hewlett Packard 5890 series equipped with a Restek Rx1-5Sil column (length 30 m, diameter 0.25 mm and film 10 μm) and an mass spectrometer (MS) Hewlett Packard 5972 series detector. The injection temperature was set to 280° C., with a split of 50:1.

Figure 4:
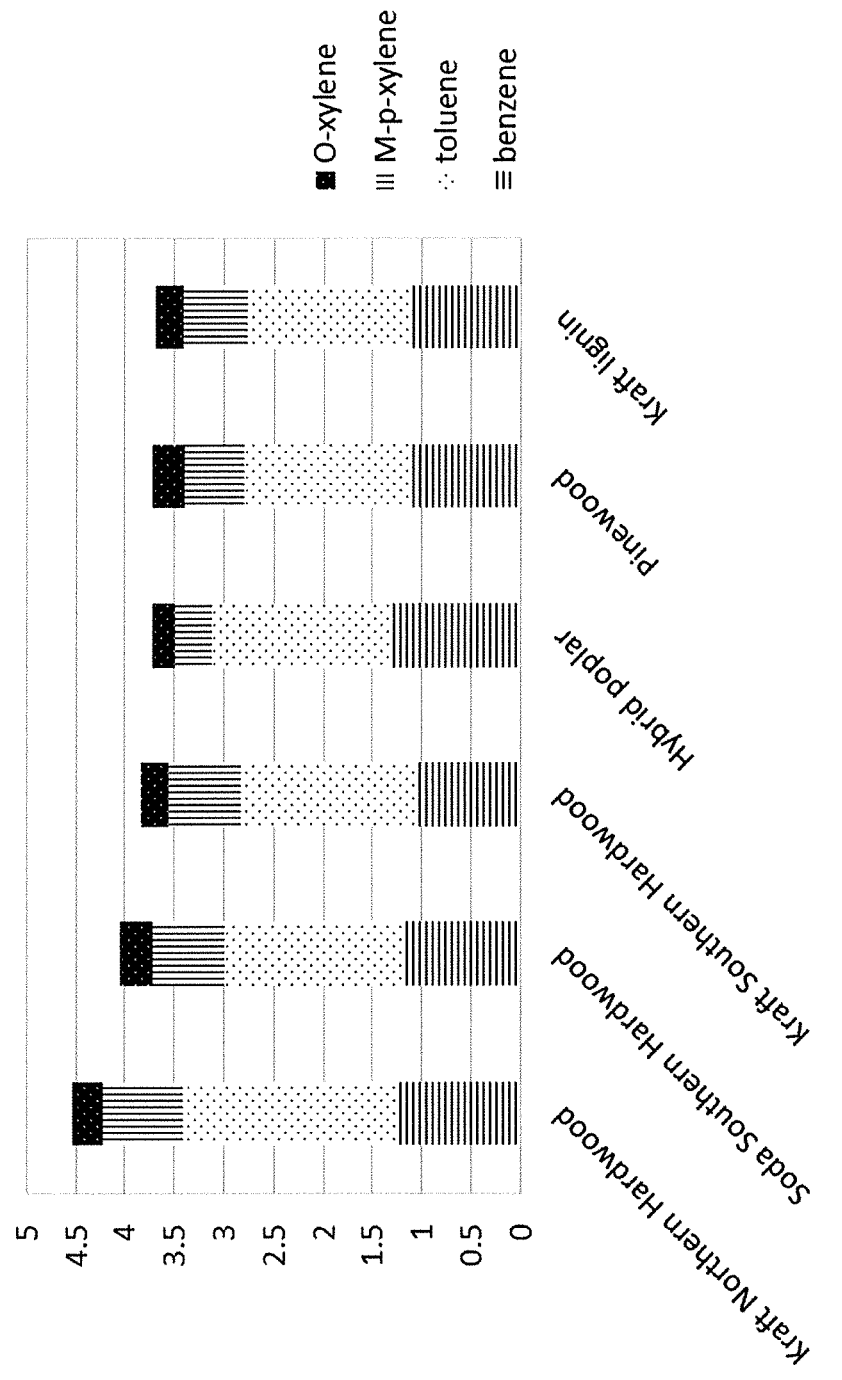
FIG. 4 shows a diagram of the results of a GC-MS analysis of small aromatic compounds in wt % of several biomass sources that have been treated according to the process of the invention. wt % is the weight of small aromatic compounds with respect to the amount of organics in the starting biomass material.

FIG. 4 shows the results of the GC-MS analysis of the several small aromatics that are formed using several biomass materials. Black liquor from hardwood has a higher yield in small aromatic compounds compared with other biomass sources.

The invention claimed is:

1. A process for the preparation of small aromatic compounds from black liquor comprising:
   adding hardwood chips and an alkaline solution to a digester and contacting the hardwood chips with the alkaline solution thereby digesting the hardwood chips to yield a cellulose pulp and a black liquor;
   adding the black liquor to a first reactor and subjecting the black liquor to a pyrolysis treatment to yield a pyrolysed black liquor gas and a solid mass comprising char and salts wherein the salts substantially derive from the treatment of black liquor;
   separating the pyrolysed black liquor gas and the solid mass and contacting at least part of the pyrolysed black liquor gas with a catalyst in a second reactor, wherein the second reactor is different from the first reactor, to provide a conversion treatment to yield a conversion product; and
   recovering small aromatic compounds from the conversion product with a condenser to form a condensed stream comprising small aromatic compounds.

2. The process according to claim 1, wherein the pyrolysis treatment is carried out without the addition of a catalyst.

3. The process according to claim 1, wherein the pyrolysis treatment of black liquor is carried out at a temperature of 350° C. to 700° C. at a pressure of between 0.1 to 6 bar(a).

4. The process according to claim 1, wherein at least a part of the solid mass is collected and heated to a temperature that is sufficiently high to recover the salt in the solid mass.

5. The process according to claim 1, wherein the conversion treatment involves the conversion of complex aromatic compounds to small aromatic compounds, the conversion of oxygen containing aromatic and oxygen containing aliphatic compounds to small aromatic compounds without oxygen atoms, and/or the conversion of hydrocarbons.

6. The process according to claim 1, wherein the conversion treatment occurs at a temperature between 200° C. and 1000° C.

7. The process according to claim 1, wherein in the conversion treatment the catalyst is present in a weight ratio of pyrolysed black liquor gas to catalyst in the range of 5:1 to 1:20.

8. The process according to claim 1, wherein the catalyst is a zeolitic catalyst selected from aluminosilicates, SAPOs, silicalites, and a combination thereof.

9. The process according to claim 1, wherein the catalyst is acidic and is made acidic by ion exchange with ammonium salts and subsequent calcination.

10. The process according to claim 1, wherein the catalyst has a silica to alumina ratio from 5 to 300.

11. The process according to claim 1, wherein the catalyst has a largest internal pore size in the range of 4.5 to 12 Å.

12. The process according to claim 1, wherein the catalyst is selected from the group consisting of ferrierite, zeolite beta, zeolite Y, zeolite X, mordenite, zeolite A, and a combination thereof.

13. The process according to claim 1, wherein the catalyst is bound by means of a binder to form a bound catalyst, and wherein the binder is selected from the group consisting of alumina, silica, silica alumina, titania, zirconia, kaolin and a mixture thereof.

14. The process according to claim 13, wherein the amount of binder in the bound catalyst is in the range of 0 to 80% by wt, based on the weight of the bound catalyst.

15. The process according to claim 1, wherein the conversion treatment is carried out in a fixed bed, moving bed or fluidized bed.

16. The process according to claim 1, wherein the recovering of aromatic compounds occurs by subjecting the condensed stream comprising small aromatic compounds to fractionation.

* * * * *